United States Patent [19]

Baret et al.

[11] Patent Number: 5,364,501
[45] Date of Patent: Nov. 15, 1994

[54] ENZYMATIC DEINKING PROCESS WITH PH SHIFT AND ADDITION OF ALKALINE CELLULASE

[75] Inventors: Jean-Luc A. G. Baret, Moret-sur-Loing; Marc Leclerc, Fontenay-aux-Roses; Jean-Pierre Lamort, Vitry-le-Francois Cedex, all of France

[73] Assignee: Novo Nordisk A/S, Bagsvaerd, Denmark

[21] Appl. No.: 934,697

[22] PCT Filed: Mar. 21, 1991

[86] PCT No.: PCT/DK91/00090
§ 371 Date: Oct. 14, 1992
§ 102(e) Date: Oct. 14, 1992

[87] PCT Pub. No.: WO91/14819
PCT Pub. Date: Oct. 3, 1991

[30] Foreign Application Priority Data

Mar. 29, 1990 [DK] Denmark ................................ 802/90

[51] Int. Cl.$^5$ ............................................. D21C 5/02
[52] U.S. Cl. ................................. 162/5; 162/7; 162/8; 162/72; 435/278
[58] Field of Search .......................... 162/5, 7, 8, 72; 435/277, 278

[56] References Cited

U.S. PATENT DOCUMENTS 4,923,565  5/1990  Fuentes et al. ................... 162/72 B
5,110,412  5/1992  Fuentes et al. ........................ 162/5

OTHER PUBLICATIONS

Orbit Search Service, File WPAT, Accession No. 88-109831/16, Honshu Paper Mfg. KK, J63059494-A, 85-315, 8816, Derwent's Abstract, Mar. 1988.
Orbit Search Service, File WPAT, Accession No. 84-051743/09, KAO Corp., J569009299-A, 840118, 8409, Derwent's Abstract, Jan. 1984.
Orbit Search Service, File WPAT, Accession No. 90-134645/18, OJI Paper KK, JP 2080683-A, 900320, 9018, Derwent's Abstract, Mar. 1990.

Primary Examiner—Karen M. Hastings
Attorney, Agent, or Firm—Steve T. Zelson; Cheryl H. Agris

[57] ABSTRACT

Good deinking of waste paper can be obtained at high consistency by first pulping at high pH, then lowering the pH, adding alkaline cellulase and letting the cellulase act during continued pulping and/or maceration. The improved deinking results in higher whiteness and better cleanliness (fewer ink particles) in paper made from the treated pulp after separation of ink particles. This cellulase treatment results in better operation of certain equipment such as thickeners and in better drainage of the pulp during paper making.

17 Claims, No Drawings they  # ENZYMATIC DEINKING PROCESS WITH PH SHIFT AND ADDITION OF ALKALINE CELLULASE

TECHNICAL FIELD

The invention relates to an enzymatic process for deinking of waste paper.

BACKGROUND ART

Waste paper, such as old newspapers and magazines, is an important raw material for the pulp and paper industry. However, the reutilization of waste paper requires special treatment to permit reincorporation into various kinds of paper.

Firstly, the waste paper must be disintegrated in water to obtain a suspension of separated fibres. Two general types of equipment for this purpose are well known in the pulp and paper industry: low-consistency pulpers operating below 5% consistency (i.e. dry substance concentration) and high-consistency pulpers operating above 8% consistency, typically at 10-20%. Due to the presence of dispersed printing ink the pulp will be grey, and it is mostly used for production of grey cardboard.

Another type of treatment consists in disintegrating printed waste paper in the presence of chemicals in order to remove the ink. This so-called deinking combines pulping with chemical action to release the ink particles from the fibres. The treatment is carried out in a pulper at alkaline conditions, the most common deinking chemicals being sodium hydroxide, sodium silicate, and hydrogen peroxide; a surfactant is also added to facilitate the removal of ink. Deinking is generally made at 30°-50° C. The pH will generally be above 9, and in case of deinking at high consistency (above 8%) a pH above 10 is usually required for satisfactory deinking. The high pH leads to some yellowing of the pulp; this is reduced by the addition of hydrogen peroxide.

After this ink-releasing step, the pulp is diluted and purified to remove various contaminants, and the ink particles are removed from the pulp by washing, flotation or a combination of these.

It is known to use alkaline cellulase to improve the deinking during low-consistency pulping. Thus, JP-A 59-9299 (Kao) describes the use of alkaline Bacillus cellulase at 3-6% consistency and 40°-45° C. The process comprises 20 minutes pulping followed by 60-90 minutes maceration. Deinking chemicals were added at the beginning of the pulping, and cellulase and surfactant were added at the beginning of pulping or at the beginning of maceration.

JP-A 63-59494 (Honshu Paper) describes the use of alkaline cellulase from *Humicola insolens* to improve deinking at 5% consistency and 50° C. The process comprises 3-5 minutes pulping followed by maceration for 140-360 minutes. Deinking chemicals, surfactant and cellulase were added before or during the maceration. The pH was 9.1.

EP 262,040 (Cellulose du Pin) and EP 351,655 (Cultor) describe the use of acidic cellulase and hemicellulase during pulping at 2-5% consistency and pH 3-7 for a different purpose (improvement of drainage). No deinking was performed.

It is described in TAPPI Journal, June 1989 that the effect of cellulase on pulp has a maximum at 3% consistency and decreases from 3 to 5%.

Use of cellulase during high-consistency pulping (above 8%) has not been described. It is the object of the invention to provide an improved process for deinking of waste paper using alkaline cellulase.

STATEMENT OF THE INVENTION

We have found that surprisingly good deinking can be obtained at high consistency by first pulping at high pH, then lowering the pH, adding alkaline cellulase and letting the cellulase act during continued pulping and/or maceration. The improved deinking results in higher whiteness and better cleanliness (fewer ink particles) in paper made from the treated pulp after separation of ink particles. Surprisingly, we have also found that this cellulase treatment results in better operation of certain equipment such as thickeners and in better drainage of the pulp during paper making, as indicated by a lower Schopper-Riegler number.

Accordingly, the invention provides an enzymatic process for deinking of waste paper, comprising the following sequential steps:

a) pulping said waste paper at a consistency above 8% in the presence of deinking chemicals at a pH above 9.5,
b) lowering the pH to 6-9.5 by addition of an acidifying agent and adding alkaline cellulase,
c) continuing the pulping and/or maceration at consistency above 8%,
d) separating ink particles from the pulp.

DETAILED DESCRIPTION OF THE INVENTION

Pulping and maceration

The consistency in steps a-c) is generally above 10%, typically 10-20%.

The duration of pulping in step a) is generally 5-30 minutes.

Step c) may comprise pulping (mechanical disintegration) or maceration (incubation with or without stirring) or a combination of these. The total duration of step c) is generally 30-120 minutes.

After the high-consistency treatment in steps a-c), the pulp may optionally be diluted to 2-6% consistency and further macerated for 15-120 minutes.

The temperature throughout the process may be 15°-60° C. typically 30°-50° C.

Pulping equipment

A conventional high-consistency pulper, used in the paper industry, can be used in practice of the invention. Pulpers equipped with a rotor or conical screw ("Helico" pulpers) from E et M Lamort, Black Clawson, Voith an other makers can be used at consistencies up to 18% (depending on the type of pulp). At consistencies above 18%, a disk pulper is preferred.

Ink separation

After the treatment in steps a-c) (and optionally further maceration at low consistency), the ink particles have been released from the fibres. The ink may then be separated from the pulp by methods known in the art. Preferred methods comprise flotation, washing or a combination of these.

After ink separation, the deinked pulp is suitable for paper making by conventional methods.

Alkaline cellulase

The invention uses an alkaline cellulase which is active and stable in the pH range 6-9.5, especially 7-9.5, and preferably one with pH optimum in this range. The invention is particularly advantageous when using a cellulase with reduced activity above pH 10, one with less than 50% activity at pH 10.5 compared to pH 9. Microbial cellulases are preferred for reasons of economy.

It is preferred to use cellulase derived from *Humicola insolens* (described in U.S. Pat. No. 4,435,307), available as Novozym 342 from Novo Nordisk A/S. Other examples are alkaline cellulase derived from Bacillus (U.S. Pat. No. 3,844,890), Aeromonas (U.S. Pat. No. 3,983,002) or Pseudomonas.

The dosage of cellulase preferably corresponds to a cellulase activity at pH 9 of 250-5000 CEVU/kg paper dry matter.

Deinking chemicals

The amount of deinking chemicals used in step a) will generally be: 0.6-1.5% of sodium hydroxide, 1-3% of sodium silicate and 0.6-1.5% of hydrogen peroxide (% of waste paper dry matter). Further, a surfactant, e.g. a nonionic one, will usually be added. The pH in step a) will normally be in the range 9.5-12, usually above 10, typically 10-11.

Acidification

The acidifying agent added in step b) can be a mineral acid such as sulphuric acid (added in the form of diluted acid). Also a salt of a strong acid and a weak base can be used, e.g. aluminium sulphate, the properties of which make it useful in the paper industry.

An organic acid (such as gluconic or citric) can also be used partly or entirely in order to adjust the balance between free calcium and sequestered calcium as needed to improve the flotation.

The pH after step b) is preferably 7-9, especially 7.5-8.5, depending on the properties of the cellulase used. In step b), the pH will usually be lowered by at least 1 unit.

Determination of brightness according to the ISO standard

This is expressed in % as the ratio of diffuse reflection of the pulp to diffuse reflection of a perfect reflector, measured by reflection in the purple to blue range centred at 457 nm (band width at half-height 44 nm).

Determination of cleanliness

This is the number of dark points on a given area of a sample of paper sheet. This may be counted visually or optico-electronically.

Determination of cellulase activity (CEVU)

A substrate solution is prepared, containing 33.3 g/l CMC (Hercules 7 LFD) in 0.1M Tris buffer at pH 9.0. The enzyme sample to be analyzed is dissolved in the same buffer. 10 ml substrate solution and 0.5 ml enzyme solution are mixed and transferred to a viscosimeter (e.g. Haake VT 181, NV sensor, 181 rpm) thermostated at 40° C. One Cellulase Viscosity Unit (CEVU) is defined as the amount of enzyme that reduces the viscosity to one half under these conditions.

Determination of pulp drainage (Schopper-Riegler)

The Schopper-Riegler number (SR) is determined according to ISO standard 5267 (part 1 ), on a homogenous pulp at a consistency of 2 g/l. A known volume of pulp is allowed to drain through a metal sieve into a funnel. This funnel has an axial hole and a side hole. The volume of filtrate that has passed through the side hole is measured in a special vessel graduated in Schopper-Riegler units.

EXAMPLE 1 (Reference)

Three different, homogenous samples of waste papers are used in comparison tests aiming at measuring the brightness of pulps deinked by two different methods. The first deinking method is a conventional chemical treatment. The second deinking method is a chemi-enzymatic treatment (named: "simultaneous enzymatic treatment") not according to the invention. The latter is characterized by the addition of the cellulase/hemicellulase enzyme preparation during paper pulping, 5 minutes after the beginning of the pulping. The enzyme action is "simultaneous" to the action of the chemicals.

Trials are realized in a 20 liters laboratory high consistency pulper, manufactured by E & M Lamort. Following pulping and maceration, the pulp is diluted to 0.8% consistency and subjected to a flotation step in a 17 liters laboratory batch flotation cell.

The results of the trials on old newspapers (Once read news, B1 quality in the European standard quality list edited by CEPAC), on high grade papers (Coloured woodfree shavings, C2), on waste magazines (Mixed pams and magazines, A6) are respectively shown in Tables 1a through 1c. It can be seen that the simultaneous enzyme action provides 2 to 3 points ISO brightness gains compared to the chemical treatment.

EXAMPLE 2

In this series of trials, three deinking methods were compared, based on the brightness of the pulps deinked: (1) by a chemical treatment, (2) by a simultaneous chemi-enzymatic treatment as described in Example 1, (3) by a "sequential enzymatic treatment" according to the invention, the latter being characterized by a pH shift during the pulping, prior to enzyme introduction into the pulp.

The waste paper used in these experiments is a well-defined, homogenous mixture of 50% high grade papers (C2) and 50% newspapers (B1). The pulping and the flotation are operated in the same conditions as in Example 1. The results are shown in Tables 2a (comparison of the chemical and the simultaneous treatment) and 2b (comparison of the chemical and the sequential treatment).

In trials 2a and 2b the control pulps (chemical treatment) have brightnesses ranging from 65 to 66.5 following deinking (the difference between 65 and 66.5 is hardly significant). When using 5 l/t enzyme in a simultaneous treatment, the brightness is enhanced by 2 to 3.5 points. This confirms Example 1 results. However, when a sequential treatment is used (2b), the brightness increase is 5.2 points compared to the control experiment. The sequential enzymatic treatment also provides more brightness gain than the simultaneous treatment with 2.5-fold less enzyme (2 l/t instead of 5 l/t).

EXAMPLE 3

Two deinking trials are realized with printed shavings (C2) as the raw material. In trial 3a (control), the waste papers are pulped at 14% consistency in a 20 liters pulper in the presence of deinking chemicals: 1% (based on dry pulp) sodium hydroxide, 2.5% sodium silicate, 1% hydrogen peroxide, 0.5% soap (Olinor 4010, Henkel-Nopco). Pulping conditions are pH 10.6 45° C./12 min. The pulp pH is then shifted to 8.5. with diluted sulfuric acid. The pulp is then diluted to 4% consistency and incubated at 50° C. for 45 minutes. The SR number is measured following this maceration, and the pulp is diluted to 0.8% consistency and subjected to flotation in a 17 liters batch flotation cell. In trial 3b the procedure is the same, except that the enzyme preparation Novozym ® 342 (545 CEVU/g) is added to the pulp following the pH shift, at the dose of 4 liters per ton of waste papers.

The results in Table 3 show that the enzyme provides a 13% SR decrease and a 3 points brightness increase.

EXAMPLE 4

The trials described in this example were realized in a pilot deinking plant (E & M Lamort) comprising: a high consistency helico pulper, a screening machine for the removal of big size impurities, a maceration tank, a micro-vortex CH cleaner, two flotation cells in a series, hydro-cyclon cleaners and an SP cleaner. The deinked pulp coming out of this equipment can be washed on a curved-screen sive. Five trials were realized in this installation with a homogenous sample of printed shavings (C2). Each trial was conducted with about 200 kg of these waste papers.

Trial no. 1 (reference): chemical deinking with 1% (based on dry pulp) sodium hydroxide, 2.5% sodium silicate, 1% hydrogen peroxide, 0.5% soap (Serfax MT90, Stephanson Bros Ltd.).

Trial no. 2 (reference): simultaneous chemi-enzymatic deinking. Chemicals dosed as in no. 1, and Novozym ® 342 (545 CEVU/g) was added after the chemicals, at the dose of 4 l/t waste papers.

Trial no. 3 (reference): chemical deinking as no. 1, but pH was shifted to 8.5 with diluted sulfuric acid following 5 min pulping.

Trial no. 4 (invention): sequential chemi-enzymatic deinking. Chemicals dosed as in no. 1, pH shifted to 8.5 as in no. 3, and Novozym ® 342 (545 CEVU/g) was added after the pH shift at the dose of 4 l/t waste papers.

Trial no. 5 (invention): same as no. 4, in order to check the repeatability.

In each trial the brightness of the pulp (Table 4b) was measured after the pulping step (5 sheets per trial), at the outlet of the flotation cells (4 sheets per trial), at the oulet of the SP cleaner (4 sheets per trial), and at the oulet of the curved-screen sieve (2 sheets per trial). The temperature, the pH and the consistency were measured at several places during each trial in order to ensure that the plant did work well. These values are shown in Table 4a.

The brightness gains provided by the use of the sequential chemi-enzymatic deinking are reproducible and significant at each process step. In trials nr. 3, 4 and 5 the brightness of the pulp at the pulper outlet is lower than in trials 1 and 2. This has been caused by a change in ink colour during pH shift; it is not related to a lower flotation efficacy, as seen in brightness values following flotation. When comparing trials 1 and 3, it seems that the flotation works better when the pH has been lowered during the pulping.

The brightness gain following flotation is around 5 points, and 3 points following cleaning. It can be seen that the washing step (curved-screen sieve) causes in all trials a significant brightness increase due to the removal of fine particles. However, the gap between the control experiments and the sequential treatment still exists (4 points), which proves that this process is compatible with either flotation or washing techniques (or a combination of the two).

TABLE 1

Comparison between the chemical and the simultaneous treatments (reference)

| | Raw material | | | | | |
|---|---|---|---|---|---|---|
| | 1a Newspaper (B1) | | 1b High grade (C2) | | 1c Magazines (A6) | |
| Treatment | Chemical | Enz. simultan. | Chemical | Enz. simultan. | Chemical | Enz. simultan. |
| Chemicals (a) | 1/2.5/1/1 | 1/2.5/1/1 | 0.6/1.2/1/0.5 | 0.6/1.2/1/05 | 0.6/1.2/1/0.5 | 0.6/1.2/1/0.5 |
| Pulping (b) | 8/45/15 | 8/45/15 | 10/45/15 | 10/45/15 | 10/45/15 | 10/45/15 |
| pH | 9.9 | 9.9 | 9.3 | 9.3 | 9.1 | 9.1 |
| Enzyme (c) | 0 | 5 | 0 | 2 | 0 | 2 |
| Maceration (d) | 8/40/90 | 8/40/90 | 10/40/45 | 10/40/45 | 10/40/45 | 10/40/45 |
| Final Iso brightness (e) | 57.5 | 60.5 | 76.5 | 79.5 | 60.0 | 62.0 |

(a): chemicals doses, % based on dry pulp, respectively: sodium hydroxide/sodium silicate/hydrogen peroxide/soap (Serfax MT90)
(b): pulping parameters, respectively: consistency (%)/temperature (°C.)/time (min)
(c): enzyme = Novozym ® 342, activity 1310 CEVU/g (l/ton waste papers)
(d): maceration parameters, respectively: consistency (%)/temperature (°C.)/time (min)
(e): brightness of the deinked pulp, measured at 457 nm (Photovolt 577 apparatus) on filter made sheets

TABLE 2

Comparison between the chemical, the simultaneous and the sequential treatments

| | 2a | | 2b | |
|---|---|---|---|---|
| Treatment | Chemical (ref.) | Enz. simultan. (ref.) | Chemical (ref.) | Enz. sequential (inven.) |
| Chemicals (a) | 1/2.5/1/1 | 1/2.5/1/1 | 1/2.5/1/1 | 1/2.5/1/1 |
| Pulping (b) | 8/45/15 | 8/45/15 | 8/45/15 | 8/45/15 |
| Enzyme (c) | 0 | 5 | 0 | 2 |
| Maceration (d) | 9/40/90 | 8/40/90 | 8/40/45 | 8/40/45 |
| pH shift | no | no | no | 7.5 |
| Final ISO brightness (e) | 65.0 | 68.5 | 66.5 | 71.7 |

(a): chemicals doses, % based on dry pulp, respectively: sodium hydroxide/sodium silicate/hydrogen peroxide/soap (Serfax MT90)
(b): pulping parameters, respectively: consistency (%)/temperature (°C.)/time (min)
(c): enzyme = Novozym ® 342, 1310 CEVU/g (l/ton waste papers)
(d): maceration parameters, respectively: consistency (%)/temperature (°C.)/time (min)
(e): brightness of the deinked pulp, measured at 457 nm (Photovolt 577 apparatus) on filter made sheets

TABLE 3

Effect of the alkaline cellulase on SR and brightness

| | 3a Control | 3b Invention |
|---|---|---|
| Pulping (a) | 14/12 | 14/12 |
| pH shift | 8.5 | 8.5 |
| Novozym ® 342 (l/t) | 0 | 4 |
| SR | 31 | 27 |
| Brightness (b) | 75.5 | 78.5 |

(a): consistency (%)/time (min)
(b): ISO brightness following flotation

TABLE 4a

| | Pilot plant parameters | | | | | | | | | | | |
|---|---|---|---|---|---|---|---|---|---|---|---|---|
| Trial no. | Pulper °C./ min. | pH pulper | T maceration °C./min. | pH maceration | T flotation 1 (°C.) | pH flotation 1 | T flotation 2 (°C.) | pH flotation 2 | Pulper consistency | Flotation consistency | SP consistency | Sieve consistency |
| 1 | 42/12 | 10.6 | 33/45 | 10.0 | 37 | 8.6 | 39 | 8.2 | 14.2% | 1.05% | 0.68% | 1.22% |
| 2 | 42/12 | 10.6 | 35/45 | 10.0 | 37 | 8.6 | 39 | 8.8 | 15.2% | 0.88% | 0.81% | 1.22% |
| 3 | 42/12 | 10.6–8.3 | 34/45 | 7.7 | 38 | 7.6 | 36 | 7.7 | 14.3% | 0.98% | 0.70% | 1.40% |
| 4 | 42/12 | 10.6–8.4 | 29/45 | 7.8 | 38 | 7.6 | 37 | 7.7 | 14.5% | 0.63% | 0.48% | 1.24% |
| 5 | 43/12 | 10.6–8.4 | 36/45 | 7.6 | 38 | 7.6 | 39 | 7.8 | 14.0% | 1.27% | 0.45% | 1.22% |

TABLE 4b

| | Pilot plant results (brightness) | | | |
|---|---|---|---|---|
| | Pulper | Flotation | SP | Sieve |
| Average Trial no. | | | | |
| 1 | 61.1 | 75.4 | 79.1 | 84.6 |
| 2 | 60.8 | 74.5 | 79.5 | 85.5 |
| 3 | 56.7 | 76.1 | 79.8 | 84.3 |
| 4 | 55.5 | 80.0 | 82.7 | 88.4 |
| 5 | 56.2 | 80.1 | 81.1 | 87.7 |
| Standard deviation Trial no. | | | | |
| 1 | 0.95 | 0.40 | 0.78 | 0.00 |
| 2 | 0.97 | 0.46 | 0.65 | 0.72 |
| 3 | 0.85 | 0.81 | 0.64 | 0.37 |
| 4 | 1.26 | 0.59 | 0.52 | 0.52 |
| 5 | 1.25 | 0.77 | 0.56 | 0.70 |

We claim:

1. An enzymatic process for deinking of waste paper, comprising the following sequential steps:
   a) pulping said waste paper at a consistency above 8% in the presence of deinking chemicals at a pH above 9.5,
   b) lowering the pH to 6–9.5 by addition of an acidifying agent and adding alkaline cellulase,
   c) continuing the pulping and/or macerating at a consistency above 8%,
   separating ink particles from the pulp.

2. The process according to claim 1, wherein the consistency in step (a) is above 10%.

3. The process according to claim 1, wherein the consistency in step (a) is 10–20%.

4. The process according to claim 1, wherein the duration of step (a) is 5–30 minutes.

5. The process according to claim 1, wherein the pH in step (a) is in the range 9.5–12.

6. The process according to claim 1, wherein the pH in step (a) is in the range 10–11.

7. The process according to claim 1, wherein the pH in step (b) is in the range 7–9.

8. The process according to claim 1, wherein the pH in step (b) is in the range 7.5–8.5.

9. The process according to claim 1, wherein the pH adjustment in step (b) is made with sulphuric acid, aluminum sulphate or an organic acid.

10. The process according to claim 9, wherein the organic acid is citric or gluconic acid.

11. The process according to claim 1, wherein the amount of cellulase added in step (b) corresponds to 250–5000 CEVU/kg of dry waste paper.

12. The process according to claim 1, further comprising addition of a hemicellulase in step (b).

13. The process according to claim 1, wherein the alkaline cellulase added in step (b) is derived from a strain of Humicola.

14. The process according to claim 1, wherein the alkaline cellulase is derived from a strain of *H. insolens*.

15. The process according to claim 1, wherein the duration of step (c) is 30–120 minutes.

16. The process according to claim 1, further comprising dilution of the pulp after step (c) to a consistency of 2–6% and maceration of the pulp for 15–120 minutes.

17. The process according to claim 1, wherein the separation of the ink particles in step (d) is performed by flotation or washing, or a combination of these.

* * * * *